US008889363B2

(12) United States Patent
Braun et al.

(10) Patent No.: US 8,889,363 B2
(45) Date of Patent: Nov. 18, 2014

(54) **METHOD FOR THE DETECTION AND IDENTIFICATION OF A VARIANT *C. DIFFICILE* STRAIN IN A SAMPLE**

(75) Inventors: Veit Braun, Mainz (DE); Karina Gisch, Mainz (DE); Michael Moos, Heidelberg (DE); Christoph von Eichel-Streiber, Schweppenhausen (DE)

(73) Assignee: BioDics, Schweppenhausen (DE)

( * ) Notice: Subject to any disclaimer, the term of this patent is extended or adjusted under 35 U.S.C. 154(b) by 703 days.

(21) Appl. No.: 12/510,013

(22) Filed: Jul. 27, 2009

(65) Prior Publication Data
US 2011/0020845 A1 Jan. 27, 2011

(51) Int. Cl.
*G01N 33/53* (2006.01)
*G01N 33/569* (2006.01)
*C07K 16/12* (2006.01)

(52) U.S. Cl.
CPC ...... *G01N 33/56911* (2013.01); *C07K 16/1282* (2013.01)
USPC .............. 435/7.1; 435/7.2; 435/7.32; 435/34; 530/387.1; 530/388.1

(58) Field of Classification Search
USPC ........ 435/7.1, 7.2, 7.32, 34; 530/387.1, 388.1
See application file for complete search history.

(56) References Cited

U.S. PATENT DOCUMENTS 6,667,035 B1   12/2003   Von Eichel-Streiber et al.

FOREIGN PATENT DOCUMENTS

DE  19739685 A1  3/1999
EP  0153519 A1   3/1984
WO  2004017899 A2  3/2004
WO  2006121422 A2  11/2006

OTHER PUBLICATIONS

Rudikoff et al (Proc Natl Acad Sci USA 1982 vol. 79 p. 1979).*
Vajdos et al. (2002) 320, 415-428.*
Chen et al. J. Mol. Bio. (1999) 293, 865-881.*
Wu et al. J. Mol. Biol. (1999) 294, 151-162.*
Blake et al., "Immunological Detection and Cytotoxic Properties of Toxins from Toxin A-Positive, Toxin B-Positive *Clostridium difficile* Variants," Journal of Medical Microbiology, vol. 53, 2004, pp. 197-205.
Rupnik, "How to Detect *Clostridium difficile* Variant Strains in a Routine Laboratory," Clinical Microbilogy & Infection, vol. 7, 2001, pp. 417-420.

* cited by examiner

*Primary Examiner* — Jennifer Graser
(74) *Attorney, Agent, or Firm* — Joyce von Natzmer; Agris & von Natzmer LLP (57) ABSTRACT

The method for detecting and identifying a variant *C. difficile* strain in a sample is characterized by the following steps: (a) obtaining a sample of excreta or tissue from a human or animal patient body; (b) bringing the sample into contact with at least one antibody from each of at least three of the antibody groups group I, group II, group III, group IV, group V and group VI; (c) detecting the antibody reaction and constructing the reaction pattern; (d) comparing the reaction pattern obtained in (c) with reference patterns from known *C. difficile* strains and *C. difficile* strains the presence of which is to be tested in the investigation test; (e) assessing the agreement between the reaction pattern obtained in (c) and the reference pattern as indicative of the presence of the *C. difficile* strain of the reference pattern concerned in the sample.

16 Claims, 8 Drawing Sheets

METHOD FOR THE DETECTION AND IDENTIFICATION OF A VARIANT C. DIFFICILE STRAIN IN A SAMPLE

BACKGROUND OF THE INVENTION

*Clostridium difficile* is an obligatory anaerobic, Gram-positive rod bacterium which is 3-6 μm long and approximately 0.5 μm wide. The *Clostridium* genus belongs to the Bacillaceae family. The discovery of *C. difficile* as an important cause of antibiotic-associated colitis occurred at the end of the 1970s. The name *C. difficile* is a reference to the slow growth in culture and difficulty with isolating the bacterium. On supplemented blood agar dishes, large translucent grey colonies grow without haemolysis. In common with all Clostridia, *C. difficile* can produce spores. In this manner, the bacteria can also survive under extreme environmental conditions.

Healthy adults have 2-7% *C. difficile* in their gastrointestinal tract. During antibiotic therapy, the protective effect of the physiological flora is perturbed and an overgrowth of *C. difficile* may occur in the gut. The resulting *clostridium difficile* associated disease (CDAD) varies in severity as a function of the virulence of the *C. difficile* strain which is present. Clinical presentation varies from mild diarrhoea to severe pseudomembranous colitis with fever and cramp-like stomach pain and the risk of severe complications such as colon perforation, sepsis and toxic megacolon. The primary virulence factors are an enterotoxin (toxin A) and a cytotoxin (toxin B). The toxins belong to the large clostridial toxin (LCT) family and have glycosyltransferase activity. Furthermore, some strains carry the genes for the binary CDT toxin (ADP-ribosyltransferase) which is considered to be a further virulence factor.

*C. difficile* strains can be divided into so-called standard strains and their variants. Strains with toxinotype 0 are generally described as standard *C. difficile* strains. These include strains with different ribotypes, for example 001, 003 and 012. Strains with toxinotype 0 are characterized by the presence of the genes for both toxins A and B, however they lack the genes for the binary toxin.

In recent years, it has been shown that in addition to standard *C. difficile* strains, there also exist a plurality of different variant *C. difficile* strains which are of growing clinical importance and which have also been detected in house pets (in particular dogs and cats) and livestock (in particular calves and pigs).

In this regard, endemic, frequently severe infections with variant *C. difficile* strains have been observed since 2003 in Canada, the USA, Great Britain and many other European states.

Isolated variant *C. difficile* strains associated with these severe infections have both the genes for toxin A (tcdA) and B (tcdB) as well as the genes for the CDT and have partial deletions in their regulatory gene tcdC.

These highly virulent *C. difficile* strains from PCR-ribotype 027, toxinotype III, REA-B1 and PFGE NAP1 have an 18 by deletion in the regulatory gene tcdC and a frameshift in position 117, presumed to be the cause of its increased toxin production in vitro and a reason for its increased virulence. These strains are also characterized in that in comparison with other *C. difficile* strains, they have altered surface proteins and increased adhesion to human gut epithelial cells. In addition, these strains are resistant to antibiotics of the fluoroquinolone class and to the antibiotic erythromycin—presumably because of mutations in the genes for gyrA/B and 23sRNA.

These highly virulent *C. difficile* strains will hereinafter be referred to by the abbreviation "C.d.-027-hv".

While earlier, an infection with *C. difficile* affected mainly patients over 60 years of age, C.d.-027-hv has also been detected in younger patients and also outside hospitals in patients deemed until now to be low risk. Compared with previously detected *C. difficile* strains, it is five times more lethal.

Another group of clinically relevant variant *C. difficile* strains is classified as ribotype 017, toxinotype VIII and serotype F. These strains are essentially characterized in that they have a 1.7 kb deletion in the tcdA gene and because of an early stop codon, they do not express toxin A. The strains have antibiotic resistance to clindamycin and fluoroquinolone, they lack the gene for the binary CDT toxin, and in addition the regulatory gene tcdC has no deletions. Increasing incidences of such strains have been reported in the USA, Japan, Israel, Ireland and the Netherlands, inter alia. The mortality in patients with such infections, at 14-66%, is higher than that for the standard strains.

These highly virulent *C. difficile* strains will hereinafter be referred to by the abbreviation "C.d.-017-hv".

Diagnostic typing of *C. difficile* is usually carried out by detecting toxin A, and in some cases by the combined detection of toxin A and toxin B. Variant *C. difficile* strains cannot be detected using this method. The variant strains are either not detected at all (toxin A negative strains) or not detected separately.

In order to identify and characterize variant *C. difficile* strains, they have to be typed. Methods for typing *C. difficile*, for example toxinotyping, serotyping, ribotyping or typing using PFGE or REA, are known in the art. All of those methods, however, are work and time intensive, can only be carried out by specialized laboratories and also require complex prior isolation of the *C. difficile* strains in question.

In order to identify specific *C. difficile* strains precisely, moreover, further investigations are usually required, such as in the case of C.d.-027-hv the detection of antibiotic resistance and of the deletion in the tcdC gene.

Therefore, in the laboratory, when for example investigating the presence of a C.d.-027-hv, the following is carried out:
1. General detection of *C. difficile* by detecting toxin A and/or B, in the stool of the patient using immunoassay;
2. if positive: culture of *C. difficile* bacteria from the material being investigated;
3. following successful isolation of bacteria: test for presence of erythromycin and moxifloxacin resistance in E-test;
4. following positive detection of resistance: test for presence of ribotype 027 using a DNA preparation and PCR amplification of ribosomal RNA gene (ribotyping) [FIG. 1];
5. following positive detection of ribotype 027: partial genotyping to detect the two toxin genes tcdA and TcdB, the cdtA/B gene for the binary CDT toxin and the deletions in the regulatory gene tcdC;
6. If both tested antibiotic resistances are present along with all the features of the characteristic genotypical pattern: diagnosis of a hypervirulent *C. difficile* ribotype 027 strain (C.d.-027-hv).

One disadvantage of previous laboratory practice which is of similar complexity for other variant and highly virulent *C. difficile* strains, lies primarily in the fact that it is very time-consuming: to isolate and culture the germ, to determine antibiotic resistance and for ribotyping, 7-10 days are required.

SUMMARY OF THE INVENTION

For optimal infection monitoring with the aim of preventing nosocomial (hospital) infections and of controlling outbreaks of infection—both to protect patients and personnel and also to save costs—the identification methods must above all be quick and as accurate as possible.

The object of the present invention is therefore to provide a method for rapid and safe detection and identification of variant C. difficile strains in a sample, in particular a sample from a patient (human or animal patient).

In particular, the problems to be solved herein are (i) the toxins of the various C. difficile strains do not differ in just one region; (ii) generating specific antibodies against LCTs of a specific C. difficile strain is not a trivial matter (for example, the EU finances a special research programme, No 37870, with acronym "EACCAD", which concerns the research of the C.d.-027-hv strains and, inter alia, is directed towards generating such antibodies against the LCTs of C.d.-027-hv); (iii) the binary toxin CDT is also formed by other C. difficile strains; and (iv) mutations in specific genes, such as tcdC, usually cannot be immunologically detected in stool samples.

The object is achieved by providing a method which is characterized by the following steps:
(a) obtaining a sample of excreta or tissue from a human or animal patient body;
(b) bringing the sample into contact with at least one antibody from each of at least three of the antibody groups group I, group II, group III, group IV, group V and group VI, wherein:
  group I comprises the following antibodies: pan-TcdB antibodies;
  group II comprises the following antibodies: antibodies which react with toxins TcdB-10463 and TcdB-017, but not with toxins TcdB-8864 and TcdB-027
  group III comprises the following antibodies: antibodies which react with TcdB-10463 but not with toxins TcdB-8864, TcdB-017 and TcdB-027
  group IV comprises the following antibodies: antibodies which react with the toxins TcdB-8864, TcdB-017 and TcdB-027 but not with toxin TcdB-10463
  group V comprises the following antibodies: antibodies which react with toxins TcdB-8864 and TcdB-027 but not with toxins TcdB-10463 and TcdB-017
  group VI comprises the following antibodies: pan-TcdA antibodies
(c) detecting the antibody reaction and constructing a reaction pattern whereby each antibody of each antibody group I to VI used in (b) is assigned a positive symbol (for example "+") for a positive detected antibody reaction and a negative symbol (for example "−") for a negative detected antibody reaction; and
(d) comparing the reaction pattern obtained in (c) with reference patterns obtained from C. difficile strains $Rx_1$, $Rx_2$, $Rx_i$ which are known in the art and are to be tested for their presence in the detection test by carrying out a reaction test between at least one of the or their large clostridial toxins $LCT\text{-}Rx_1$, $LCT\text{-}Rx_2$, $LCT\text{-}Rx_i$ and the antibodies from at least three of the antibody groups I to VI selected in step (b), and wherein the reaction results obtained for each LCT and the at least three antibody groups from groups I to VI are detected or recorded or set down in a pattern so that each antibody group is assigned either a positive symbol (for example "+") in the event of a positive detected antibody reaction; a negative symbol (for example "−") in the event of a negative detected antibody reaction;
(e) assessing the match between the reaction pattern obtained in (c) and a reference pattern as indicative of the presence of the C. difficile strain having the reference pattern concerned in the sample.

The abbreviations used herein have the following meanings:
LCT: large clostridial toxin, namely toxin A and/or toxin B from C. difficile;
TcdB-10463: toxin B from C. difficile strain VPI-10463 (="standard toxin");
TcdB-8864: toxin B from C. difficile strain 8864;
TcdB-1470: toxin B from C. difficile strain 1470;
TcdB-7002/8: toxin B from C. difficile strain 7002/8;
TcdB-017: toxin B from C. difficile strains with ribotype 017;
TcdB-027: toxin B from C. difficile strains with ribotype 027;
pan TcdA-antibody: antibody which recognizes tcdA proteins from all pathogenic C. difficile strains (for example TTC 8);
pan TcdB-antibody: antibody which recognizes TcdB-proteins from all pathogenic C. difficile strains (for example 2CV, TGC 35).

The teaching of the method according to the invention is based on the surprising finding that:
(1) the antibodies directed against the LCTs from C. difficile, namely against toxin A or toxin B, can be divided into six groups which are characterized as follows:
  Group I=pan-TcdB antibody TGC 35, which is produced by the hybridoma cell line deposited at the DSMZ (German Collection of Microorganisms and Cell Cultures, Inhoffenstraβe 7B, 38124 Braunschweig, Germany) on 5 Jun. 2008 under accession number DSM ACC 2918 and monoclonal 2 CV, which is produced by the hybridoma cell line deposited at the DSZ (German Collection of Microorganism and Cell Cultured, Inhoffenstra βe 7B, 38124 Braunschweig, Germany) on 5 Jun. 2008 under accession number DSM ACC 2321 and antibodies which are identical to TGC 35 and/or 2CV in function and/or effect;
  Group II=Antibodies which react with the standard toxin TcdB-10463 and the variant TcdB-017, but not with the variant toxins TcdB-8864 and TcdB-027, in particular antibody TGC 23, which is produced by the hybridoma cell line deposited at the DSMZ (German Collection of Microorganisms and Cell Cultures, Inhoffenstraβe 7B, 38124 Braunschweig, Germany) on 5 Jun. 2008 under accession number DSM ACC 2917, and antibodies which are identical to TGC 23 in function and/or effect;
  Group III=antibodies which react with the standard toxin TcdB-10463 but not with the variant toxins TcdB-8864, TcdB-017 and TcdB-027, in particular antibody TGC 41, which is produced by the hybridoma cell line deposited at the DSMZ (German Collection of Microorganisms and Cell Cultures, Inhoffenstraβe 7B, 38124 Braunschweig, Germany) on 5 Jun. 2008 under accession number DSM ACC 2919, and antibodies which are identical to TGC 41 in function and/or effect;
  Group IV=antibodies which react with the variant toxins TcdB-8864 and TcdB-017 and TcdB-027 but not with the standard toxin TcdB-10463, in particular antibody TGC 16, which is produced by the hybridoma cell line deposted at the DSMZ (German Collection of Microorganisms and Cell Cultures, Inhoffenstraβe 7B, 38124 Braunschweig, Germany) on 5 Jun. 2008 under accession number DSM ACC 2915, and antibodies which are identical to TGC 16 in function and/or effect;

Group V=antibodies which react with the variant toxins TcdB-8864 and TcdB-027 but not with the standard toxin TcdB-10463 and the variant TcdB-017, in particular antibody TGC 19, which is produced by the hybridoma cell line deposited at the DSMZ (German Collection of Microorganisms and Cell Cultures, Inhoffenstraße 7B, 38124 Braunschweig, Germany) on 5 Jun. 2008 under accession number DSM ACC 2915, and antibodies which are identical to TGC 19 in function and/or effect;

Group VI=pan-TcdA antibodies which react with the tcdA proteins of all pathogenic C. difficile strains, in particular antibody TTC 8, which is produced by the hybridoma cell line deposited at the DSMZ (German Collection of Microorganisms and Cell Cultures, Inhoffenstraße 7B, 38124 Braunschweig, Germany) on 23 Jun. 1997 under accession number DSM ACC 2322, and antibodies which are identical to TTC 8 in function and/or effect (such as the PCG4 antibody described in U.S. Pat. No. 4,879,218); and (2) that the currently known virulent variant C. difficile strains or their LCTs each exhibit a characteristic reaction pattern with the antibodies of these six groups—in particular their toxin B with the antibodies of the five groups I to V—which differs from the reaction pattern of toxins from other (highly) virulent variant C. difficile strains and from the reaction patterns of toxins from the standard C. difficile strains.

As an example, the highly virulent C. difficile strain C.d.-027-hv is characterized by the reaction pattern "+--+++" in the group sequence I, II, III, IV, V, VI, while the equally highly virulent C. difficile strain C.d.-017-hv is characterized by the reaction pattern "++-+--" (also in the group sequence I, II, III, IV, V, VI).

In order to identify and detect the various currently known and diagnostically relevant virulent variant C. difficile strains, at least one antibody from each of at least three different antibody groups is usually necessary and sufficient. As an example, in order to distinguish the C. difficile strain C.d.-027-hv from the other relevant variant C. difficile strains and from the standard C. difficile strains, the reaction pattern for the three groups II, IV and VI, namely "-++" (in the group sequence II, IV, VI) is sufficient, while in order to distinguish or identify the C. difficile strain C.d.-017-hv, the reaction pattern of the three groups II, IV and VI, namely "++-" (also in the group sequence II, IV, VI) is sufficient.

Particular advantages of the method of the invention are as follows:

A direct determination can be obtained from a stool sample by means of a test which is simple to carry out and takes just a few hours of whether or not a specific highly virulent variant C. difficile strain is present: if, for example, the presence of C.d.-027-hv is being investigated and if an antibody-antigen reaction pattern is obtained that indicates no positive reaction for an antibody of at least one of antibody groups I, IV, V and/or VI, then it can be reliably concluded that no C.d.-027-hv type strain is present. On the other hand, if the antibody-antigen reaction pattern indicates a positive reaction for all four antibody groups I, IV, V and VI, then it is highly probable that an infection with a C.d.-027-hv strain is present. Then, to confirm the suspected diagnosis, the time-consuming and expensive special analyses of antibiotic resistance, ribotyping and/or genetic analysis (in particular detection of the toxin genes tcdA, tcdB and tcdA/B and the regulatory gene tcdC with the characteristic deletions and frame shifts) could/should be carried out.

In other words: the method of the invention replaces the first three steps in the current investigation method (toxin detection, bacterial culture, antibiotic resistance test) and allows after a much shorter period, namely a few hours, as opposed to the current period of several days a conclusive subsequent diagnosis in cases where no infection with the variant C. difficile strains under investigation, for example C.d.-027-hv, is present. The time-consuming and expensive further steps (4, 5 and 6) in the current investigation method then only need to be carried out if the method of the invention indicates the presence of the variant C. difficile strain in question, for example C.d.-027-hv or C.d.-017-hv.

In addition, preventative measures, for example isolation, quarantine, strict hygiene measures, can then be introduced in a focussed manner if it transpires that the risk of a C.d.-027-hv infection or C.d.-017-hv infection, as indicated by the results of the detection tests of the invention, is actually high.

The antibodies of groups I to VI are preferably monoclonal antibodies. Basically, antibodies for the method of the invention may be any natural antibody or any antibody which has been produced by biotechnology or gene technology, for example camel antibodies (nanobodies), affibodies, anticalins, or cystein knot mini proteins.

In one embodiment of the method, which has proved to be very good, the at least one antibody from group I is the monoclonal antibody 2CV, which is produced by the hybridoma cell line deposited at the DSMZ (German Collection of Microorganisms and Cell Cultures, Inhoffenstraße 7B, 38124 Braunschweig, Germany on 23 Jul. 1997 under accession number DSM ACC 2321 or the monoclonal antibody TGC 35, which is produced by the hybridoma cell line deposited at the DSMZ (German Collection of Microorgsnisms and Cell Cultures, Inhoffenstraße 7B, 38124 Braunschweig, Germany) on 5 Jun. 2008 under accession number DSM ACC 2918 and/or the at least one antibody from group II is the monoclonal antibody TGC 23, which is produced by the hybridoma cell line deposited at the DSMZ (German Collection of Microorganisms and Cell Cultures, Inhoffenstraße 7B, 38124 Braunschweig, Germany) on 5 Jun, 2008 under accession number DSM ACC 2917 and/or the at least one antibody from group III is the monoclonal antibody TGC 41, which is produced by the hybridoma cell line deposited at the DSMZ (Germany Collection of Microorgsnisma and Cell Cultures, Inhoffenstraße 7B, 38124 Braunschweig, Germany) on 5 Jun. 2008 under accession number DSM ACC 2919 and/or the at least one antibody from group IV is the monoclonal antibody TGC 16, which is produced by the hybrisoma cell line deposited at the DSMZ (Germany Collection of Micoorganisms and Cell Cultures, Inhoffenstraße 7B, 38124 Braunschweig, Germany) on 5 Jun. 2008 under accession number DSM ACC 2915 and/or the at least one antibody from group V is the monoclonal antibody TGC 19, which is produced by the hybridoma cell line deposited at the DSMZ (Germany Collection of Microorganisms and Cell Cultures, Inhoffenstraße 7B, 38124 Braunschweig, Germany) on 5 Jun. 2008 under accession number DSM ACC 2916 and/or the at least one antibody from group VI is the monoclonal antibody TTC 8, which is produced by the hybridoma cell line deposited at the DSMZ (Germany Collection of Micoorganisms and Cell Cultures, Inhoffenstrße 7B, 38124 Braunschweig, Germany) on 23 Jul. 1997 under accession number DSM ACC 2322.

In practice the excreta sample is preferably a stool sample and the tissue sample is preferably a blood sample.

A further embodiment of the method, which is highly relevant in practice as it allows variant C. difficile strains to be detected rapidly and reliably, is characterized in that in step (b) the sample is brought into contact with an antibody from each of groups I, IV and VI and in that in step (c) a positive reaction of the antibodies from groups I, IV and VI indicates the presence of a highly virulent, variant *C. difficile* strain.

An embodiment of the method which is highly relevant in practice and which allows rapid and reliable detection of the highly virulent *C. difficile* strain ribotype 027, PFGE-NAP1, REA-B1 and toxinotype III and thus allows suspected cases of C.d.-027-hv to be tested, is characterized in that in step (b) the sample is brought into contact with at least one antibody from each of the antibody groups group II, group IV and group VI and in that in step (c) a positive reaction of the antibodies from group IV and group VI and a negative reaction of the antibody(ies) from group II indicates the presence of a highly virulent variant *C. difficile* strain of type ribotype 027, PFGE-NAP1, REA-B1 and toxinotype III.

This embodiment can be further extended in that in step (b) the sample is also brought into contact with at least one antibody of antibody group I and/or antibody group III and/or antibody group V and in that in step (c) in addition, a positive reaction of the antibody(ies) from group I and group V and a negative reaction of the antibody(ies) from group III indicates the presence of a highly virulent variant *C. difficile* strain of type ribotype 027, PFGE-NAP1, REA-B1 and toxinotype III.

In a further embodiment of the method, which is highly relevant for practice and which allows rapid and reliable detection of the highly virulent *C. difficile* strain ribotype 017, toxinotype VIII and serotype F and thus allows the testing of suspected cases of C.d.-017-hv, is characterized in that in step (b) the sample is brought into contact with at least one antibody from each of the antibody groups group II, group IV and group VI, and in that in step (c) a positive reaction of the antibodies from group II and group IV and a negative reaction of the antibody(ies) from group VI indicates the presence of a highly virulent variant *C. difficile* strain of type ribotype 017, toxinotype VIII and serotype F.

This embodiment can be further extended in that in step (b) the sample is additionally brought into contact with at least one antibody from antibody group I and/or antibody group III and/or antibody group V, and in that in step (c) in addition, a positive reaction of the antibody(ies) from group I and a negative reaction of the antibodies from group III and group V indicate the presence of a highly virulent variant *C. difficile* strain of type ribotype 017, toxinotype VIII and serotype F.

The object of the present invention is also achieved by the provision of the monoclonal antibody which is produced by the hybridoma cell line deposited at the DSMZ, (German Collection of Microorganisms and Cell Cultures, Inhoffenstraße 7B, 38124 Braunschweig, Germany) on 5 Jun. 2008 with accession number DSM ACC 2916 (TGC 19), and which is suitable and intended for use in the method of the invention to detect and identify variant *C. difficile* strains, in particular in the variation of the method for the detection and identification of the *C. difficile* strain ribotype 027, PFGE-NAP1, REA-B1 and toxinotype III.

The stated object is also achieved by the provision of the monoclonal antibody which is produced by the hybridoma cell line deposited at the DSMZ, (Germany Collection of Microorganisms and Cell Cultures), Inhoffenstraße 7B, 38124 Braunschweig, Germany) on 5 Jun. 2008 with accession number DSM ACC 2917 (TGC 23), and which is suitable and intended for use in the method of the invention to detect and identify variant *C. difficile* strains, in particular in the variation of the method for the detection and identification of the *C. difficile* strain ribotype 017, toxinotype VIII and serotype F.

The object of the present invention is also achieved by the provision of the monoclonal antibody which is produced by the hybridoma cell line deposited at the DSMZ,(German Collection of Microorganisms and Cell Cultures, Inhoffenstraße 7B 38124 Braunschweig, Germany) on 5 Jun. 2008 with accession number DSM ACC 2915 (TGC 16), and which is suitable and intended for use in the method of the invention to detect and identify a variant *C. difficile* strain in a sample, in particular in the variation of the method for the detection and identification of *C. difficile* strains with ribotype 017, toxinotype VIII and serotype F and/or *C. difficile* strains with ribotype 027, PFGE-NAP1, REA-B1 and toxinotype III.

Finally, the stated object is also achieved with the provision of the monoclonal antibody which is produced by the hybridoma cell line deposited at the DSMZ, (Germany Collection of Microorganisms and Cell Cultures, Inhoffenstraße 7B, 38124 Braunschweig, Germany) with accession number DSM ACC 2918 (TGC 35), and which is suitable and intended for use in the method of the invention to detect and identify a variant *C. difficile* strain in a sample, in particular in the method variation for the detection and identification of *C. difficile* strains with ribotype 017, toxinotype VIII and serotype F and/or *C. difficile* strains with ribotype 027, PFGE-NAP1, REA-B1 and toxinotype III.

The invention will now be described in more detail with reference to the following examples:

DETAILED DESCRIPTION OF VARIOUS AND PREFERRED EMBODIMENTS

Figure 1:
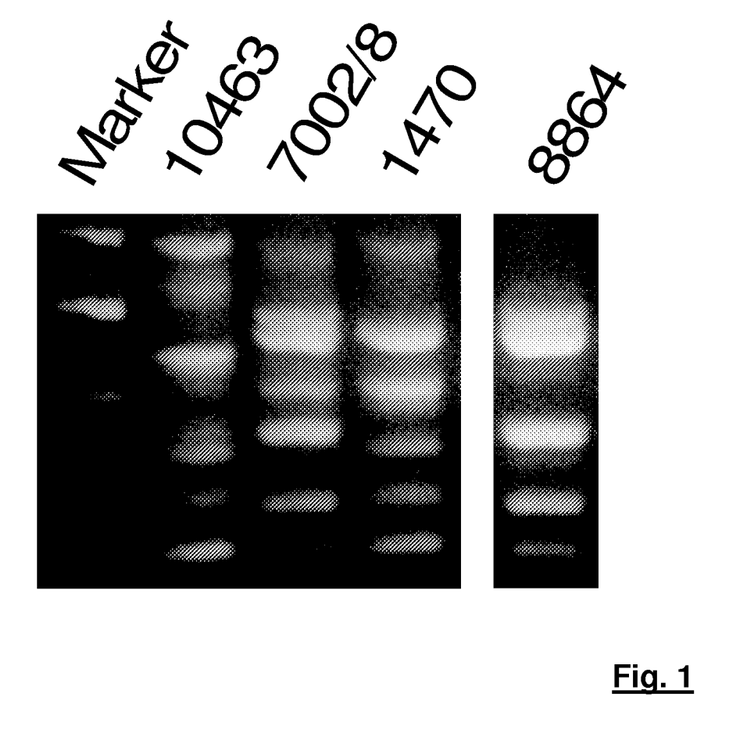
FIG. 1: Ribotyping of the strains employed.

The Figures mentioned in the examples show the following:

FIG. 1: Ribotyping of the strains employed: The strains were ribotyped as described by Stubbs et al. and were assigned the various ribotypes by comparison with reference strains. In this respect, strain VPI-10463 and strain 8864 were determined to be ribotypes which were unknown until now and strain 1470 and strain 7002/8 were denoted as ribotype 027. The marker bands ran at 600 bp, 500 bp, 400 by and 300 by (from the top).

Figure 2:
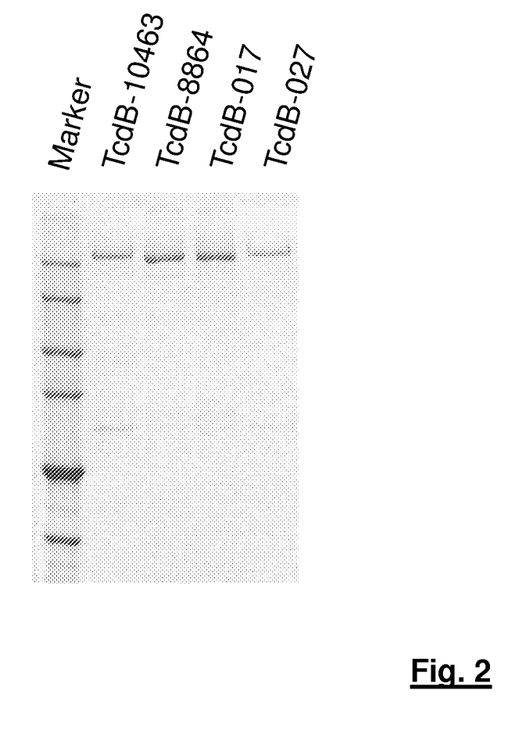
FIG. 2: Purified toxin B variants.

FIG. 2: Purified toxin B variants. Various toxin B variants are shown in Coomassie stained SDS PAGE. 250-400 ng of the individual toxins was applied per track.

Figure 3:
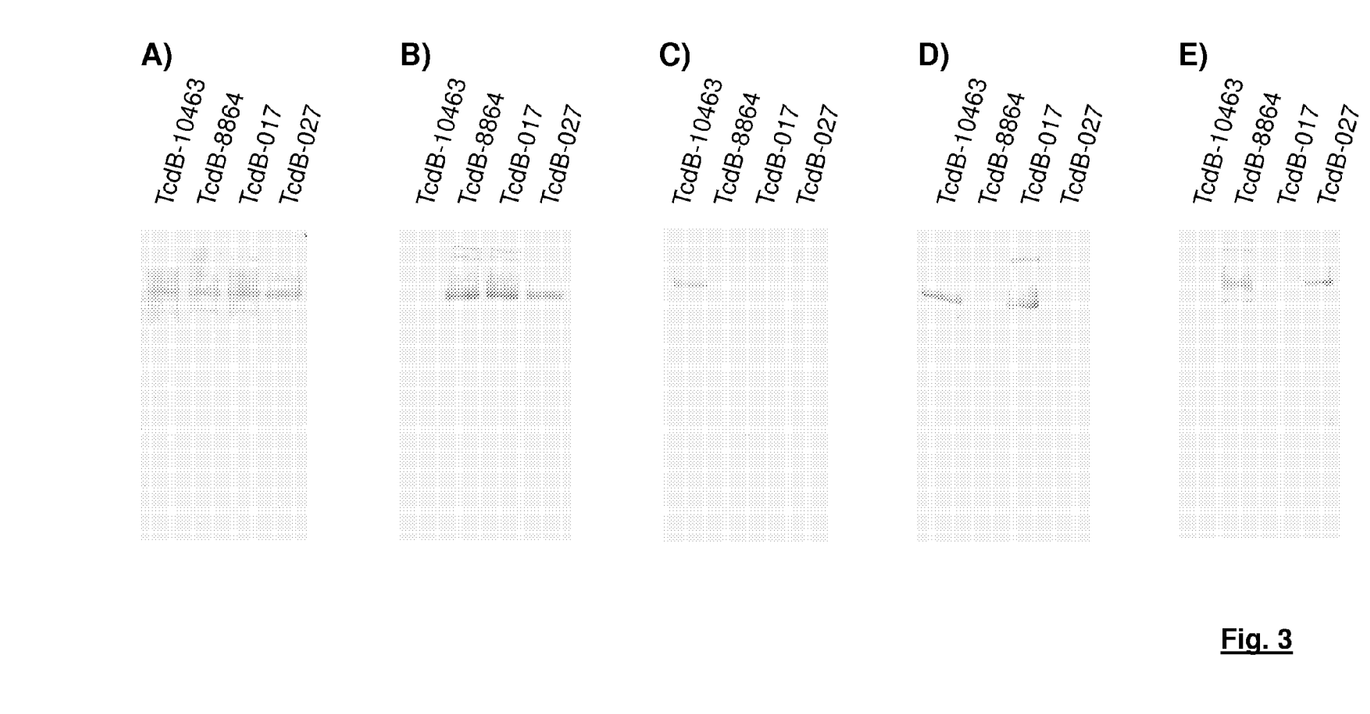
FIG. 3: Proof of specificity of monoclonal anti toxin B antibodies.

FIG. 3: Proof of specificity of monoclonal anti toxin B antibodies. Various toxin B variants were separated in SDS PAGE, blotted on nylon membranes and then developed with the corresponding antibodies. The specificities of the monoclonal antibodies TGC 35 (FIG. 3A), TGC 16 (FIG. 3B), TGC 41 (FIG. 3C), TGC 23 (FIG. 3D) and TGC 19 (FIG. 3D) are shown.

Figure 4:
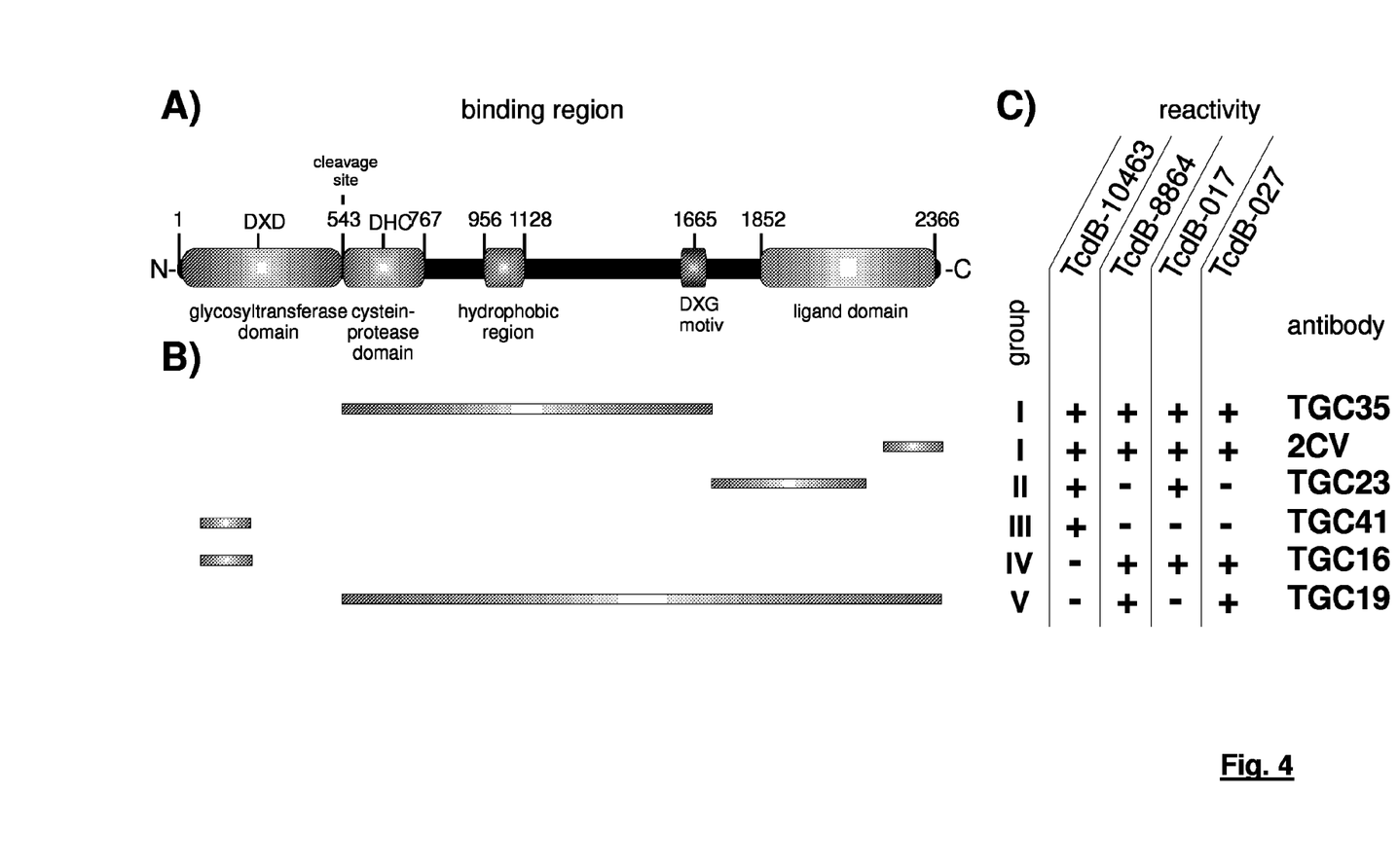
FIG. 4: Binding region for monoclonal antibodies.

FIG. 4: Binding region for monoclonal antibodies. FIG. 4A is a schematic illustration of the structure of toxin B. FIG. 4B indicates the binding region for the antibody within toxin B. FIG. 4C shows the reactivities of the monoclonal antibodies.

Figure 5:
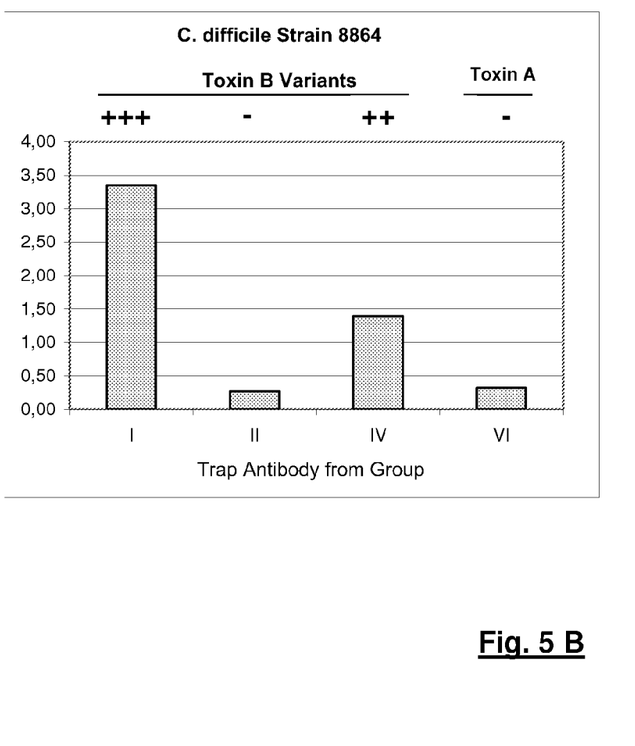
FIG. 5: Reference pattern for *C. difficile* strains.

FIG. 5: Reference pattern for *C. difficile* strains. Toxin A and toxin B expression in the culture supernatant from four different *C. difficile* strains was tested using sandwich ELISA and using trap antibodies from antibody groups I, II, IV and VI. The following trap antibodies were used: group I: TGC 35; group II: TGC 23; group IV: TGC 16; group VI: TTC 8. The recognition pattern for *C. difficile* strains VPI-10463 (FIG. 5A), 8864 (FIG. 5B), 1470 ribotype 017 (FIG. 5C) and 7002/8 ribotype 027 (FIG. 5D) are shown.

Figure 6:
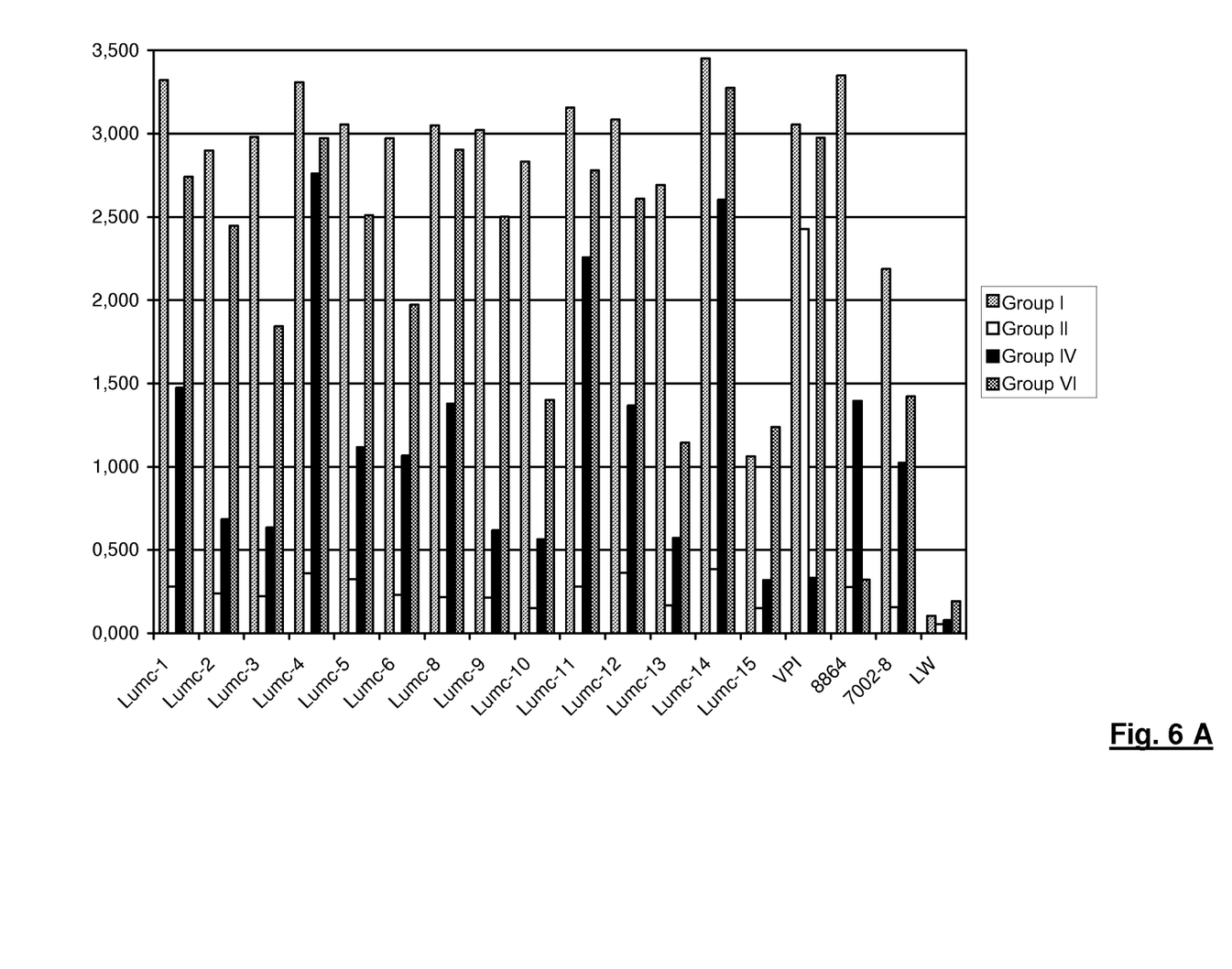
FIG. 6: Reaction pattern of various *C. difficile* strains in trap ELISA.

FIG. 6: Reaction pattern of various *C. difficile* strains in trap ELISA. The identification antibodies used were TGC 35 for group I, TGC 23 for group II, TGC 16 for group IV and TTC 8 for group VI. FIG. 6A shows the results from 17 different *C. difficile* strains and FIG. 6B shows the results from further *C. difficile* strains.

EXAMPLE 1

Generation of Monoclonal Antibodies which React Specifically with Toxin B from *C. difficile*

(A) Production of Purified *C. difficile* Toxin B from Various *C. difficile* Strains
The following *C. difficile* strains were used:
VPI-10463 (ATCC 43255),
8864 (CCUG 20309),
1470 (ATCC 43598), and
7002/8 (human isolate from a sample from a patient)

The strains were ribotyped in accordance with the ribotyping method described by Stubbs et al in 1999. The results obtained are shown in FIG. 1. It becomes obvious that strain 1470 corresponds to ribotype 017 and strain 7002/8 to ribotype 027, while strains VPI-10463 and 8864 must be assigned to as yet not officially named ribotypes.

The toxin B (TcdB-10463) expressed by strain VPI-10463 is generally described in the art as standard toxin.

Strain 8864 produces a variant of this toxin B (TcdB-8864) which differs from the standard toxin primarily in the C-terminal receptor binding domain (Soehn et al, 1998).

Strain 1470 expresses a toxin B (TcdB 1470) which differs from the standard toxin B particularly in the N-terminal enzymatic domain (from Eichel-Streiber et al, 1995).

The sequence of toxin B of strain 7002/8 ribotype 027 is not known. In contrast, the sequences of the TcdB-027 in two other C.d.-027-hv strains have been determined (strain QCD-32g58, GenBank-Acc No NZ_AML00000000, strain R20291, www.sanger.ae.uk). A comparison of this TcdB-027 sequence with the standard toxin B and other variant TcdB toxins shows that TcdB-027 regarding the N-terminal enzymatic domain is similar to the standard toxin TcdB-10463, but regarding the C-terminal domain is similar to the variant toxin TcdB-8864.

To purify the toxins, the bacteria were cultured anaerobically in brain heart infusion nutrient medium (Becton Dickinson, Heidelberg, Germany). Next, toxins A and B were purified from the supernatant from these cultures, as described by Moos et al (2000). The purity of the toxins was monitored in Coomassie gel (see FIG. 2).

The isolated and purified TcdB from *C. difficile* strains VPI-10463, 8864 and 1470 were inactivated using methods which are known and routine in the art and the success of inactivation was checked using a cytotoxicity test.
(B) Generation of Monoclonal Antibodies Against Toxin B Variants from (A)

In a series of experiments, each time several mice were initially primary immunized and then had two boosters with the inactivated toxin B variants TcdB-8864 and TcdB-1470 and the standard toxin TcdB 10163.

The animals' titre against the immunogen was determined and if a significant titre had developed the spleen was removed. The isolated spleen cells were fused with the mouse myeloma cell line X63Ag8.653 (ATCC CRL 1580) using known and routine methods and the fusion cells were then selected and cloned. The hybridoma clones obtained were screened immunologically for the production of specific monoclonal antibodies against the toxin B used for immunization.

In total, 15 fusions were carried out and finally, 21 different hybridoma cell lines were isolated which specifically expressed toxin B antibodies.

For the further investigations, the antibodies were purified from the cell culture supernatant. To this end, the hybridoma cell lines were grown in serum-free ISF-1 medium (Biochrom, Berlin, Germany) and then cultivated in a volume of 250 ml in a spinner system (Bellco, Vineland, USA) at 50 rpm until the vitality of the culture fell to below 30%. The culture supernatant was purified using a protein A column (HiTrap MabSelect SuRe, GE Healthcare, Freiburg, Germany). The concentration of the purified antibodies was 1-2 mg/ml; the purity was checked in Coomassie gel.

EXAMPLE 2

Characterization of Anti-toxin B Antibodies

In order to characterize the antibodies generated in Example 1, they were tested using Western blot.

To this end, initially each time 250-400 ng of standard toxin B 10463 and the toxin B variants TcdB-8864, TcdB-017 and TcdB-027 were separated in SDS PAGE and then blotted in a semi-dry blotting procedure on nylon membranes. They were developed using routine methods which are known in the art.

In order to detect the toxins, the monoclonal antibodies generated in Example 1 were used.

The results for the antibodies with the laboratory references TGC 16, TGC 19, TGC 23, TGC 35 and TGC 41 are summarized in FIG. 3.

The results show that most of the generated antibodies recognize a sub group of various toxin B variants rather than a particular mono-specific toxin variant.

In total 11 different antibodies were identified which bind to the standard toxin B and to all toxin B variants. A characteristic representative of this so-called pan-TcdB antibodies is the antibody TGC 35. The hybridoma cell line which produces this TGC 35 was deposited at the DSMZ (German collection of Microorganisms and Cell Cultures, Inhoffenstraβe 7B, 38124 Braunschweig, Germany) on 5 Jun. 2008 with accession number DSM ACC 2918.

Some antibodies react both with the standard toxin and with the toxin TcdB-017. A characteristic representative of this antibody group is antibody TGC 23. The hybridoma cell line which produces this TGC 23 was deposited with the DSMZ, (German Collection of Microorganisms and Cell Cultures, Inhofenstraβe 7B, 38124 Braunschweig, Germany) on 5 Jun. 2008 with accession number DSM ACC 2917.

Some antibodies react specifically with the standard toxin TcdB-10463. A characteristic representative of this antibody group is antibody TGC 41. The hybridoma cell line which produces this TGC 41 was deposited with the DSMZ (Germany Collection of Microoganisms and Cell Cultures, Inhofenstraβe 7B, 38124 Braunschweig, Germany) on 5 Jun. 2008 with accession number DSM ACC 2919.

Surprisingly, two antibodies could be generated which react with one or more of the toxin B variants, but not with the standard toxin B. The antibody TGC 16 does not bind to the standard toxin B but with the variant toxins TcdB-8864, TcdB-017 and TcdB-027. The hybridoma cell line which produces this TGC 16 was deposited with the DSMZ (Germany Collection of Microorganisms and Cell Cultures, Inhoffenstraße 7B, 38124 Braunschweig, Germany) on 5 Jun. 2008 with accession number DSM ACC 2915.

The antibody TGC 16 does not bind to the standard toxin B but with the variant toxins TcdB-8864, TcdB-017 and TcdB-027. The hybridoma cell line which produces this TGC 16 was deposited with the DSMZ on 05 Jun. 2008 with accession number DSM Acc 2915.

Antibody TGC 19 does not bind to the standard toxin B or the variant toxin TcdB-017, but does bind to the variant toxins TcdB-8864 and TcdB-027. The hybridoma cell line which produces this TGC 19 was deposited with the DSMZ (Germany Collection of Microorganisms and Cell Cultures, Inoffenstraße 7B, 38124 Braunscweig, Germany) on 5 Jun. 2008 with accession number DSM ACC 2916.

The antibodies were investigated in a trap ELISA for their antigen detection threshold. To this end, 50 µl of coating buffer (50 mM $Na_2CO_3$, 50 mM $NaHCO_3$, pH 9.6) and 250 ng of the respective antibody per well were incubated at room temperature for 3 h in ELISA plates and thus the antibodies were fixed on the ELISA plate. Non-specific binding sites were blocked by subsequent incubation with 200 µl 5×WAPU (12.5 ml Triton X100, 62.5 ml 1M Tris-HCl, pH 7.5, 62.5 ml of a 20% gelatine solution, qsp 500 ml with $H_2O$) for a period of 30 minutes. Next, various concentrations of the antigens, namely in the case of TGC 16 and TGC 19 the antigen TcdB-027 and in the case of TGC 23 and TGC 35 the antigen TcdB-017, were applied. Detection was carried out with polyclonal serum (266 ng/ml). The reaction results (not shown here) showed that for the antibodies TGC 16 and TGC 23, the detection limit for the respective toxin B was at <300 pg/ml, for antibody TGC 35 it was less than 1 ng/ml and for antibody TGC 19 it was 1 ng/ml.

The antibodies TGC 16, TGC 19, TGC 23, TGC 35 and TGC 41 were investigated to find their binding sites to toxin B. Protein fragments of toxin B were produced by proteoltyic digestion of toxin B or by cloning and expression of recombinant toxin B partial fragments in *E coli*. These toxin B partial fragments were separated in Western blot experiments and the blots were then incubated with the antibodies TGC 16, TGC 19, TGC 23, TGC 35 and TGC 41. The results of these tests are summarized schematically in FIG. 4 and show that the individual antibodies recognize or bind various regions of the toxin B molecule:

All amino acid positional data are given with respect to the corresponding positions in the standard toxin TcdB-10463.

TGC 16 binds TcdB-8864, TcdB-017 and tcdB-027 each within the glycosyl transferase domain in the region of amino acid positions 122 to 261.

TGC 19 binds TcdB-8864 and tcdB-027 each in the domain outside the glycosyl transferase domain between amino acid positions 543 and 2366.

TGC 23 binds standard toxin and TcdB-017 each in the ligand domain distanced from the C-terminal end between amino acid positions 1692 and 2113.

TGC 35 binds standard toxin, TcdB-8864, TcdB-017 and TcdB-027 each within the translocation domain between the glycosyl transferase domain at the N-terminal end of the toxin and the ligand domain at the C-terminal end between amino acid positions 543 and 1692.

TGC 41 binds standard toxin in an analogous manner to TGC 16, i.e. within the glycosyl transferase domain in the region of amino acid positions 122 to 261.

TGC 16 and TGC 41 bind in the same toxin B region, namely in the glycosyl transferase domain, however from various toxin B variants, namely from standard toxin (TGC 41) on one hand and on the other hand from TcdB-8864, TcdB-017 and TcdB-027 (TGC 16). Thus, a region in toxin B has been identified for the first time which allows a specific differentiation between the standard toxin B TcdB-10463 and the variant toxins TcdB-8864, TcdB-017 and Tcd-027. Surprisingly, this region is the glycosyl transferase domain which determines the enzymatic activity of toxin B. The enzymatic activity is generally the same with all B toxins.

The novel antibodies generated in the context of the present invention allow different groups (classes) of antibodies (antibody groups/antibody classes) to be constructed which differ as regards their reactivity with standard toxin B and with the various toxin B variants:

The pan TcdB antibody group will hereinafter be ascribed to group I. Typical representatives of this group are the monoclonal antibodies TGC 35 and 2CV (known from EP-0 994 904).

The group of those antibodies which react both with the standard toxin and with the toxin TcdB-017 but not with the variant toxins TcdB-027 and TcdB-8864 will hereinafter be ascribed to group II. A typical representative of this group is the monoclonal antibody TGC 23.

The group of those antibodies which react with the standard toxin TcdB-10463 but not with the variant toxins TcdB-027, TcdB-8864 and TcdB-1470 will hereinafter be ascribed to group III. A typical representative of this group is the monoclonal antibody TGC 41.

The group of those antibodies which do not interact with the standard toxin B but do interact with the toxins TcdB-8864, TcdB-017 and TcdB-027 will hereinafter be ascribed to group IV. A typical representative of this group is the monoclonal antibody TGC 16.

The group of those antibodies which do not react with the standard toxin B or the toxin TcdB-017 but do react with the toxins TcdB-8864 and TcdB-027 will hereinafter be ascribed to group V. A typical representative of this group is the monoclonal antibody TGC 19.

Further, the group known as the pan TcdA specific antibodies is known from the literature, which will hereinafter be ascribed to group VI. A typical representative of this group is the monoclonal antibody TTC 8 (known from EP-0 994 904).

EXAMPLE 3

Detection of LCTs in trap ELISA—Construction of Antigen-antibody Reference Patterns for known Variant *C. difficile* Strains Using Antibody Groups I, II, IV and VI Antigen-antibody reference patterns were basically carried out as follows: at least toxin B, preferably both large clostridial toxins (LCTs), were obtained (in the form of a culture supernatant or purified toxin) from *C. difficile* strains $Rx_1$, $Rx_2$, $Rx_i$ which were known in the art and which were to be tested for their presence in the detection test. These known toxins $LCT-Rx_1$, $LCT-Rx_2$, $LCT-Rx_i$ were used to carry out a reaction test with at least one antibody preferably from each of antibody groups I to VI. The reaction results obtained for each LCT ($LCT-Rx_1$, $LCT-Rx_2$, $LCT-Rx_i$) and the antibody groups employed were set out in a pattern whereby each antibody group was assigned either a positive symbol (for example "+") if a positive antibody reaction was detected or a negative symbol (for example "−") if a negative antibody reaction was detected.

Specifically, in the present example the following was carried out:

ELISA plates were covered as follows with the purified antibodies described in Example 2, namely TGC 35 (group I), TGC 23 (group II), TGC 16 (group IV) and TTC 8 (group VI): per well 50 µl of coating buffer (50 mM $Na_2CO_3$, 50 mM $NaHCO_3$, pH 9.6) containing 250 ng of the respective antibody was incubated for 3 h at room temperature and thus the antibody was attached to the ELISA plates. Next, non specific binding sites were blocked by incubation with 200 µl 5×WAPU (12.5 ml TritonX100, 62.5 ml 1M Tris-HCl, pH 7.5, 62.5 ml of a 20% gelatine solution, qsp 500 ml with $H_2O$) for a period of 30 minutes.

The C. difficile strains 10463, 8864, 1470 and 7002/8 were grown as described in Example 1, and 50 µl aliquots of the culture supernatant was added to the microtitre plates coated with the antibodies. Non-specifically bound proteins were removed by washing three times with TBST (150 mM NaCl, 10 mM Tris, 0.05% Tween20, pH 8.0). Next, any toxins bound to the antibodies were detected with 50 µl of polyclonal anti-toxin B serum (266 ng/ml) in trap ELISA. Development was carried out using alkaline phosphatase in a standard procedure.

The results of this ELISA are shown graphically in FIG. 5. FIG. 5 demonstrates that each of the four different C. difficile strains displayed a unique characteristic reaction pattern with the four antibodies used, which reaction pattern differs from those of the other strains:

The supernatant from strain VPI-10463 reacts positively with antibodies TGC 35/group I, TGC 23/group II and TTC 8/group VI and negatively with TGC 16/group IV (see FIG. 5A).

The supernatant from strain 8864 reacts positively with the antibodies TGC 35/group I and TGC 16/group IV and negatively with TGC 23/group II and TTC 8/group VI (see FIG. 5B).

The supernatant from strain 1470 (ribotype 017) reacts positively with antibodies TGC 35/group I, TGC 23/group II and TGC 16/group IV and negatively with TTC 8/group VI (see FIG. 5C).

The supernatant from strain 7002/8 (ribotype 27) reacts positively with the antibodies TGC 35/group I, TGC 16/group IV and TTC 8/group VI and negatively with TGC 23/group II (see FIG. 5D).

Checking these results in a simultaneous test with toxin B from C. difficile strains with ribotype 027 and various combinations of antibodies from antibody groups I to VI confirmed that TcdB-027 always reacts positively with antibodies from groups I, IV, V and VI and always reacts negatively with antibodies from groups II and III.

In other words: the reaction pattern "+−−+++" for toxin B from an unknown C. difficile strain with antibodies from the six antibody groups in the group sequence group I, group II, group III, group IV, group V, group VI means that it can be concluded that the unknown C. difficile strain is a ribotype -027, into which category the highly virulent C.d.-027-hv strain also falls.

Checking these results in a simultaneous test with toxin B from C. difficile strains with ribotype 017 and various combinations of antibodies from antibody groups I to VI confirmed that TcdB-017 always reacted positively with antibodies from groups I, II and IV and always reacted negatively with antibodies from groups III, V and VI.

In other words: the reaction pattern "++−+−−" for toxin B from an unknown C. difficile strain with antibodies from the six antibody groups in the group sequence group I, group II, group III, group IV, group V, group VI means that it can be concluded that the unknown C. difficile strain is a ribotype -017, into which category the highly virulent C.d.-017-hv strain also falls.

EXAMPLE 4

Identification of C. difficile Ribotypes Using Antigen-antibody Reaction Reference Patterns To construct the antigen-antibody reaction reference pattern, the procedure of Example 3 was carried out.

To construct the sample-specific reaction pattern, the following was carried out: the C. difficile strain to be investigated was cultivated using known methods and the supernatant or the purified toxins were tested. To this end, at least one antibody from at least two, preferably three or four of groups I, II, III, IV, V or VI, for example antibodies TGC 16, TGC 19, TGC 23, TGC 41, TGC 35 and TTC 8, were applied to a suitable surface, for example a membrane, using methods which are well known to the skilled person.

Next, the sample was brought into contact with these antibodies, hereinafter termed identification antibodies. Suitable methods for this purpose are known to the skilled person, for example ELISA or lateral flow methods such as that described in EP-1 143 248.

At the end of the method-specific reaction time the or each reaction batch was freed from non-bound sample material (washed).

In order to detect which identification antibody displayed an antigen-antibody reaction with the sample and which had not reacted, a detection antibody was used. Detection antibodies which can be used are polyclonal sera against toxin A and toxin B (monospecific or cross-reactive), or antibodies from one or more of groups I, II, III, IV, V or VI. When selecting the detection antibody, care must be taken that its target epitope differs from the target epitope of the identification antibody or is present in each toxin in such a majority that the detection antibody can bind into a complex with the identification antibody. The detection antibodies are labelled with suitable markers such as colloidal gold, carbon or latex particles or enzymatic markers such as HRP (horse radish peroxidase) or alkaline phosphatase.

The detection antibody is either added to the reaction batch prior to application of the sample or together with the sample or after expiry of the method-specific reaction time between the identification antibody and the sample.

Since at the end of the method-specific reaction time sample toxin which is not bound to the identification antibody and any contaminating proteins present are removed (washed away), a marker signal (positive signal "+") only occurs when a complex of identification antibody, sample toxin and detection antibody has been formed.

The marker signals "+" or "−" obtained for each identification antibody are placed in the reaction pattern. Such a reaction pattern may, for example, look like FIG. 5A. Comparison with the reference patterns in this case leads to the conclusion (or suspected diagnosis) that the C. difficile strain VPI-10463 is present.

If the reaction pattern looks like FIG. 5B, for example, comparison with the reference patterns leads to the conclusion (or suspected diagnosis) that the C. difficile strain 8864 is present. If the reaction patterns looks like FIG. 5C, for example, comparison with the reference patterns leads to the conclusion (suspected diagnosis) that the C. difficile strain 1470 or a C. difficile strain with ribotype 017 is present. If the reaction pattern looks like FIG. 5D, for example, comparison with the reference patterns leads to the conclusion (suspected diagnosis) that the C. difficile strain 7002/8 or a C. difficile strain with ribotype 027 is present.

EXAMPLE 5

Analysis of Various *C. difficile* Strains with Antibodies from Groups I, II, IV and VI In the experiment below, the method of the invention was used to identify and detect variant *C. difficile* strains using a series of strains with known ribotype, namely 19 strains with ribotype 027 (Lumc-1, Lumc-2, Lumc-3, Lumc-4, Lumc-5, Lumc-6, Lumc-8, Lumc-9, Lumc-10, Lumc-11, Lumc-12, Lumc-13, Lumc-14, Lumc-16, Lumc-17, Lumc-19, Lumc-20, Lumc-21, 7002-42), 4 strains with ribotype 017 (Lumc-22, Lumc-23, Lumc-40, Lumc-41), two strains from ribotype 001 (7002-29, 7002-43) and one strain from ribotype 014 (Lumc-31). The reference strains were the strains VPI-10463, 8864 and 7002/8. Antibodies from groups I, II, IV and VI were used in a trap ELISA and the resulting reaction patterns were compared with the constructed reference patterns (see Example 3).

The various *C. difficile* strains were cultured, as described in Example 1 and the supernatant was used in the subsequent experiments. The identification antibodies used were the antibodies TGC 35 (group I), TGC 23 (group II), TGC 16 (group IV) and TTC 8 (group VI) as described in Example 3 and were fixed on the ELISA plates. To this end, 250 ng/well of TGC 23, 128 ng/well of TGC 16 and TGC 35, as well as 1 µg/well of TTC 8 were used and the plates were then washed in PBS.

In order to carry out the ELISA tests, the non specific binding sites on the plates were blocked initially by incubating for 1 h at 37° C. in PBS+3% BSA. Next, 50 µl/well of the supernatant from the *C. difficile* cultures were applied and the plates were once again incubated for 1 h at 37° C. Non-bound proteins were removed by washing three times with PBS+3% BSA. The detection antibody used in the case of TGC 35, TGC 16 and TGC 23 was biotin-labelled polyclonal antitoxin B serum (0.32 µg/ml). When detecting toxin A, the antibody TTC 8 in the biotinylated form was also used as the detection antibody. After washing again with PBS+3% BSA, 50 µl of streptavidin-HRP (0.1 µg/ml, Pierce, Rockford, USA) per well was added and the plates were incubated for 1 h at 37° C. Next, the plates were washed with PBS and developed using 50 µl/well TMB (1-step Ultra TMB, Pierce, Rockford, USA). The plates were incubated for 30 min at room temperature in the dark and the reaction was then stopped with 100 µl/well of 2M $H_2SO_4$. Assessment was carried out at OD450 against a blank. The cut-off was set at 0.5.

The results of this test are shown graphically in FIGS. 6A and 6B:

in 19 different strains, the reaction pattern "+−++" was detected in the group sequence I, II, IV and VI;

in 4 different C.d.-017-hv strains, the reaction pattern "+++−" was detected in the group sequence I, II, IV and VI. Analysis of the 017 strains indicated that in vitro, the strains produced relatively little toxin (even the TGC signal was relatively weak). It was clear, however, that a specific reaction between the antibody TGC 23 (DSM ACC 2917) and the toxin B-017 occurred only in these strains. While in all other supernatants (i.e. all C.d.-027-hv strains, as well as all tested ribotype 001 strains) in the case of using the detection antibody TGC 23 the values were not over 0.4, with C.d.-017-hv strains, the absorption was clearly over the cutoff threshold of 0.5.

The results confirm that the antigen-antibody reaction pattern "+−++" in the group sequence I, II, IV and VI leads to the conclusion that the strain under investigation is a C.d.-027-hv strain and the reaction pattern "+++−" in the group sequence I, II, IV and VI leads to the conclusion that a C.d.-017-hv strain is present.

List of Cited Literature

Moos et al. (2000) "Purification and evaluation of large clostridial cytotoxins that inhibit small GTPases of Rho and Ras subfamilies"Meth Enzymol. 325: 114-125.

Soehn et al. (1998) "Genetic rearrangement in the pathogenicity locus of *Clostridium difficile* strain 8864—implications for transcription, expression and enyzmatic activity of toxin A and B"Mol Gen Genet. 258: 222-232.

Stubbs et al (1999) "PCR targeted to the 16-23rRNA gene intergenic space region of *Clostridium difficile* and construction of a library of 116 different PCR ribotypes"Clin Microbiol 37: 461-463.

von Eichel-Streiber et al. (1995) "Closing in on the toxic domain through analysis of a variant *Clostridium difficile* cytotoxin B"Mol Microbiol 17: 313-321.

What is claimed is:

1. A method for detecting and identifying a variant *C. difficile* strain in a sample, comprising:
    (a) obtaining a sample of excreta or tissue from a body;
    (b) bringing the sample into contact with at least one antibody from each of at least three of antibody groups group I, group II, group III, group IV, group V and group VI to detect a positive or a negative reaction with the sample, wherein:
    group I consists of pan-TcdB antibody TGC 35 (DSM ACC 2918), pan-TcdB antibody 2CV (DSM ACC 2321) and/or antibodies which bind to the same binding sites on purified TcdB protein from all pathogenic *C. difficile* strains as said antibody TGC 35 and/or 2CV;
    group II consist of antibody TGC 23 (DSM ACC 2917) and/or antibodies which bind to the same binding sites on purified toxins TcdB-10463 and TcdB-017 as said antibody TGC 23
    group III consists of antibody TGC 41 (DSM ACC 2919) and/or antibodies which bind to the same binding sites on purified toxin TcdB-10463 as said antibody TGC 41;
    group IV consists of antibody TGC 16 (DSM ACC 2915) and/or antibodies which bind to the same binding sites on purified toxins TcdB-8864, TcdB-017 and TcdB-027 as said antibody TGC 16;
    group V consists of antibody TGC 19 (DSM ACC 2916) and/or antibodies which bind to the same binding sites on purified toxins TcdB-8864 and TcdB-027 as said antibody TGC 19;
    group VI consists of antibody TTC 8 (DSM ACC 2322) and/or antibodies which bind to the same binding sites on purified pan-TcdA proteins from all pathogenic *C. difficile* strains as said antibody TTC 8;
    (c) detecting an antibody reaction and constructing a reaction pattern for said at least three of the antibody groups I to VI of (b), wherein a positive symbol signifies a positive detected antibody reaction and a negative symbol signifies a negative detected antibody reaction; and
    (d) comparing a reaction pattern obtained in (c) with reference patterns which are obtained for said at least three of the antibody groups of (c) which are obtained from known *C. difficile* strains Rx1, Rx2, Rxi whose presence is being ascertained by carrying out a reaction test between at least one of their large clostridial toxins (LCT) LCT-Rx1, LCT-Rx2, LCT-Rxi and the antibodies from said at least three antibody groups I to VI of (c), wherein the reaction results obtained for each LCT and said at least three antibody groups are recorded in a pattern so that each antibody group is assigned either a positive symbol ("+") in case of a positive detected antibody reaction or a negative symbol ("−") in case of a negative detected antibody reaction; and (e) assessing whether a match between the reaction pattern obtained in (c) and one of the reference patterns in (d) exists, and (f) determining the presence of the *C. difficile* strain of the reference pattern in the sample.

2. The method according to claim 1, wherein the antibodies are monoclonal antibodies.

3. The method according to claim 1, wherein
in (b) the sample is brought into contact with at least one antibody from each of groups I, IV and VI; and
in (c) a positive reaction of the antibodies from groups I, IV and VI indicates presence of a highly virulent variant *C. difficile* strain.

4. The method according to claim 1, wherein
in (b) the sample is brought into contact with at least one antibody from each of antibody groups group II, group IV and group VI; and in that
in (c) a positive reaction of antibodies from group IV and group VI and a negative reaction of the antibody(ies) from group II indicate the presence of the highly virulent variant *C. difficile* strain ribotype 027, PFGE-NAP1, REA-B1 and Toxinotype III.

5. The method according to claim 4, wherein
in (b) the sample is additionally brought into contact with at least one antibody from antibody group I and/or antibody group III and/or antibody group V; and in that
in (c) in addition, a positive reaction of the antibody(ies) from group I and group V and a negative reaction of the antibody(ies) from group III indicate the presence of the highly virulent variant *C. difficile* strain ribotype 027, PFGE-NAP1, REA-B1 and Toxinotype III.

6. The method according to claim 1, wherein
in (b) the sample is brought into contact with at least one antibody from each of antibody groups group II, group IV and group VI; and in that
in (c) a positive reaction of the antibodies from group II and group IV and a negative reaction of the antibody(ies) from group VI indicate the presence of the highly virulent variant *C. difficile* strain ribotype 017, toxinotype VIII and serotype F.

7. The method according to claim 6, wherein
in (b) the sample is additionally brought into contact with at least one antibody from antibody group I and/or antibody group III and/or antibody group V; and
in (c) in addition, a positive reaction of the antibody(ies) from group I and a negative reaction of the antibodies from group III and group V indicate the presence of the highly virulent variant *C. difficile* strain ribotype 017, toxinotype VIII and serotype F.

8. The method of claim 5, wherein the group V antibody is a monoclonal antibody produced from a hybridoma cell line deposited with the DSMZ, Braunschweig, Germany having accession number DSM ACC 2916 (TGC 19) and wherein *C. difficile* strain ribotype 027, PFGE-NAP1, REA-B1 and toxinotype III are detected and identified.

9. The method of claim 4, wherein the group II antibody is a monoclonal antibody produced from a hybridoma cell line deposited with the DSMZ, Braunschweig, Germany having accession number DSM ACC 2917 (TGC 23) and wherein *C. difficile* strain ribotype 017, toxinotype VIII and serotype F are detected and identified.

10. The method of claim 4, wherein the group IV antibody is a monoclonal antibody produced from a hybridoma cell line deposited with the DSMZ, Braunschweig, Germany having accession number DSM ACC 2915 (TGC 16) and wherein *C. difficile* strain with ribotype 017, toxinotype VIII and serotype F and/or with ribotype 027, PFGE-NAP1, REA-B1 and toxinotype III are detected and identified.

11. The method of claim 5, wherein the group I antibody is a monoclonal antibody produced from a hybridoma cell line deposited with the DSMZ, Braunschweig, Germany having accession number DSM ACC 2918 (TGC 35) and wherein *C. difficile* strains with ribotype 017, toxinotype VIII and serotype F and/or with ribotype 027, PFGE-NAP1, REA-B1 and toxinotype III are detected and identified.

12. Method according to claim 1, wherein in step (b) the sample is brought into contact with at least one antibody from each of groups II, IV and VI and wherein the sample is further brought into contact with antibodies from group I, wherein group I consists of pan-TcdB antibodies.

13. Method according to claim 1, wherein in step (b) the sample is brought into contact with at least one antibody from each of groups II, IV and VI and wherein the sample is further brought into contact with antibodies from group III, wherein group III consists of antibodies which react with TcdB-10463, but not with toxins TcdB-8864, TcdB-017 and TcdB-027.

14. Method according to claim 1, wherein in step (b) the sample is brought into contact with at least one antibody from each of groups II, IV and VI and wherein the sample is further brought into contact with antibodies from group V, wherein group V consists of antibodies which react with toxins TcdB-8864 and TcdB-027, but not with toxins TcdB-10463 and TcdB-017.

15. The method of claim 1, wherein the variant *C. difficile* strain detected and identified in the sample is ribotype 027 or ribotype 017.

16. The method of claim 1, wherein in (c) the positive symbol "+" signifies a positive detected antibody reaction and the negative symbol "−" signifies a negative detected antibody reaction.

* * * * *